United States Patent
Badoux et al.

(10) Patent No.: US 10,703,849 B2
(45) Date of Patent: Jul. 7, 2020

(54) HMF OLIGOMERS

(71) Applicant: AVALON Industries AG, Zug (CH)

(72) Inventors: Francois Badoux, Unteraegeri (CH);
Stephan Koehler, Constance (DE);
Mariangela Mortato, Basel Stadt
(CH); Stefan Krawielitzki,
Holzhaeusern (CH)

(73) Assignee: AVALON Industries AG, Zug (CH)

( * ) Notice: Subject to any disclaimer, the term of this patent is extended or adjusted under 35 U.S.C. 154(b) by 119 days.

(21) Appl. No.: 15/904,814

(22) Filed: Feb. 26, 2018

(65) Prior Publication Data

US 2018/0244823 A1    Aug. 30, 2018

(30) Foreign Application Priority Data

Feb. 27, 2017 (EP) .................................. 17158249

(51) Int. Cl.

| | | |
|---|---|---|
| *C08G 2/14* | (2006.01) | |
| *C08G 61/12* | (2006.01) | |
| *B27N 3/02* | (2006.01) | |
| *B32B 21/04* | (2006.01) | |
| *C08G 2/10* | (2006.01) | |
| *C09J 161/02* | (2006.01) | |
| *C08G 6/00* | (2006.01) | |
| *C08L 97/02* | (2006.01) | |
| *B27N 3/00* | (2006.01) | |
| *C07D 307/50* | (2006.01) | |

(Continued)

(52) U.S. Cl.
CPC ............. *C08G 2/10* (2013.01); *B27N 3/002* (2013.01); *B27N 3/02* (2013.01); *B32B 21/04* (2013.01); *C07D 307/50* (2013.01); *C07D 407/06* (2013.01); *C08G 6/00* (2013.01); *C08G 61/125* (2013.01); *C08G 65/36* (2013.01); *C08L 97/02* (2013.01); *C09J 161/02* (2013.01); *C08G 2261/344* (2013.01)

(58) Field of Classification Search
CPC ........................................................ C08G 2/14
USPC ........................................................ 528/270
See application file for complete search history.

(56) References Cited

U.S. PATENT DOCUMENTS

| | | |
|---|---|---|
| 2,776,948 A | 1/1957 | Snyder |
| 2,937,158 A | 5/1960 | Snyder |

(Continued)

FOREIGN PATENT DOCUMENTS

| | | |
|---|---|---|
| AU | 2017243162 A1 | 11/2018 |
| DE | 10 2014 112 240 A1 | 3/2016 |

(Continued)

OTHER PUBLICATIONS

European Office Action in EP 17158247.1-1302, dated Jun. 13, 2017, with English translation of relevant parts.

(Continued)

*Primary Examiner* — Duc Truong
(74) *Attorney, Agent, or Firm* — Collard & Roe, P.C.

(57) ABSTRACT

Carbon-linked 5-hydroxymethylfurfural (HMF) oligomers contain at least one first HMF unit and one second HMF unit. The first and second HMF units are linked by a carbon-carbon bond with involvement of an aromatically bound carbon atom at position 3 or 4 of the furan ring of the first HMF unit. The HMF oligomers may be used as reactive carbonyl compounds in the manufacture of thermally curable resins on the basis of phenolic compounds and/or aminoplastic forming agents as well as in the manufacture of wood composite products.

8 Claims, 2 Drawing Sheets

(51) Int. Cl.
*C07D 407/06* (2006.01)
*C08G 65/36* (2006.01)

(56) References Cited

U.S. PATENT DOCUMENTS

| | | |
|---|---|---|
| 4,048,126 A | 9/1977 | Gibbons et al. |
| 4,524,164 A | 6/1985 | Viswanathan et al. |
| 4,692,478 A | 9/1987 | Viswanathan et al. |
| 9,416,030 B2 | 8/2016 | Vyskocil et al. |
| 2008/0207795 A1 | 8/2008 | Henry et al. |
| 2013/0150597 A1 | 6/2013 | Backes et al. |
| 2013/0345450 A1 | 12/2013 | Böhling et al. |
| 2014/0371473 A1 | 12/2014 | Blank et al. |
| 2015/0083358 A1 | 3/2015 | Joke et al. |
| 2016/0102165 A1 | 4/2016 | Hsieh et al. |

FOREIGN PATENT DOCUMENTS

| | | |
|---|---|---|
| WO | 2015/123781 A1 | 8/2015 |
| WO | 2017/168108 A1 | 10/2017 |

OTHER PUBLICATIONS

European Office Action in EP 17158248.9-1302, dated Jun. 14, 2017, with English translation of relevant parts.
European Office Action in EP 17158249.7-1302, dated Jun. 8, 2017, with English translation of relevant parts.
Wikipedia, "Phenol formaldehyde resin," retrieved Feb. 22, 2018, pp. 1-4 https://en.wikipedia.org/wiki/Phenol_formadehyde_resin.
Esmaeili, N. et al. "Hydroxymethyl furfural-modified urea-formaldehyde resin: synthesis and properties" Published online Jun. 24, 2016, Eur. J. Wood Prod., DOI 10.1007/s0017-016-1072-8, 10 pages.
Patil et al., "Comparison of Structural Features of Humins Formed Catalytically from Glucose, Fructose, and 5-Hydroxymethylfurfuraldehyde", Energy & Fuels, American Chemical Society, 2012, pp. 5281-5293 (13 pages).
Putten et al., "Hydroxymethylfurfural, A Versatile Platform Chemical Made from Renewable Resources", Chemical Reviews, American Chemical Society, 2013, pp. 1499-1597 (99 pages).
Mija et al., "Humins as promising material for producing sustainable carbohydrate-derived building materials", Construction and Building Materials, 2017, pp. 594-601 (8 pages).

HMF OLIGOMERS

CROSS REFERENCE TO RELATED APPLICATION

Applicant claims priority under 35 U.S.C. § 119 of European Application No. 17158249.7 filed Feb. 27, 2017, the disclosure of which is incorporated by reference.

BACKGROUND OF THE INVENTION

1. Field of the Invention

The present invention relates to new hydroxymethylfurfural (HMF) oligomers and to processes for the manufacture of such oligomers. The present invention relates in particular to new carbon-linked HMF oligomers. These oligomers are useful as reactive carbonyl compounds in the manufacture of thermally curable resins on the basis of phenolic compounds and/or aminoplastic forming agents as well as in the manufacture of wood composite materials.

2. Description of the Related Art 5-hydroxymethylfurfural (HMF)

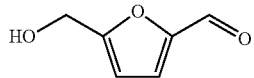

is an important platform chemical and has attained considerable significance as a starting compound for numerous syntheses. In addition, it is known that, in the manufacture of thermally curable resins on the basis of phenolic compounds and/or aminoplastic forming agents, reactive carbonyl compounds such as formaldehyde, which are hazardous to health, can be replaced at least partly by HMF. In the trade magazine European Journal of Wood Products, an HMF-modified urea-formaldehyde resin is described. For the manufacture of this resin up to approximately 30 wt % of the formaldehyde was replaced by purified, crystalline HMF (N. Esmaeili et al., DOI 10.1007/s0017-016-1072-8).

The occurrence of linear and branched oligomers in solutions of HMF is known, for example, from DE 10 2014 112 240 A1. The HMF oligomers are formed, among other examples, during the manufacture of HMF from carbohydrates and carbohydrate-containing biomass under hydrothermal conditions, and can be detected by nuclear magnetic resonance (NMR) spectroscopy, infra-red (IR) spectroscopy and mass spectroscopy. In addition, their formation may be followed using high-performance liquid chromatography (HPLC) analyses.

Already known oligomeric compounds from HMF result from the linking of aldehyde and/or hydroxyl groups of individual HMF monomers or individual monomers with HMF oligomers consisting of HMF monomers. The HMF monomers ultimately represent the units of the formed HMF oligomers. The HMF oligomers are linear or more or less highly branched and have ether, hemiacetal and/or acetal bonds. HMF oligomers are formed both under acidic conditions and under basic conditions.

Linear HMF oligomers usually contain structural elements that comprise units of the type

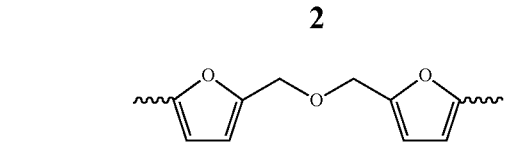

linked by ether bonds, and/or units of the type

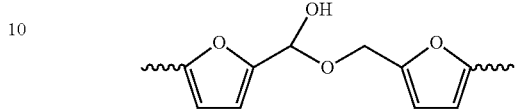

linked by formation of hemiacetals. In addition, branched HMF oligomers may contain structural elements with units of the type

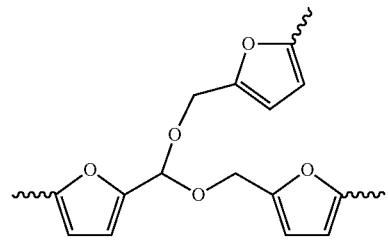

linked to form acetals. In this connection, the curved lines mean that the illustrated structural elements are a part of an HMF oligomer. An HMF oligomer usually has several identical or different structural elements of the indicated types. Terminal HMF units are bounded by aldehyde groups or hydroxymethyl groups.

SUMMARY OF THE INVENTION

The inventors have found that, besides HMF oligomers with the ether, hemiacetal and/or acetal bonds, carbon-linked HMF oligomers, in which units are linked by a carbon-carbon bond, are formed both under acid and under basic conditions. As an example, these bonds may be formed during an electrophilic attack of an aldehyde group of a first HMF monomer or of an HMF unit of an HMF oligomer at the carbon atom in position 3 or 4 of a furan ring of a second HMF monomer or of an HMF unit of an HMF oligomer.

In one aspect, the present invention therefore provides new carbon-linked HMF oligomers, which contain at least one first HMF unit and one second HMF unit, and which are characterized in that first and second HMF units are linked by a carbon-carbon bond with involvement of an aromatically bound carbon atom at position 3 or 4 of the furan ring of the first HMF unit. In a further aspect, the present invention provides a process for the manufacture of carbon-linked HMF oligomers that treats an aqueous suspension of cellulose-containing biomass and/or an aqueous carbohydrate solution of at least one hexose and/or one aqueous 5-hydroxymethylfurfural solution under hydrothermal conditions. An additional aspect of the present invention provides a process for the manufacture of carbon-linked HMF oligomers that exposes a more or less pure solution of HMF monomers and/or HMF oligomers to condition that lead to the formation of HMF oligomers.

BRIEF DESCRIPTION OF THE DRAWINGS

Other objects and features of the invention will become apparent from the following detailed description considered In the drawings.

DETAILED DESCRIPTION OF PREFERRED EMBODIMENTS

In contrast to the HMF monomers, compounds from at least two linked HMF units/monomers are designated as "HMF oligomers" within the meaning of the present invention. In this context, the transition between HMF oligomers and HMF polymers is continuous. Within the meaning of the present invention, "HMF oligomers" are understood as compounds with a molar mass of up to 3000 g/mol.

Within the meaning of the present invention, HMF oligomers are designated as "carbon-linked HMF oligomers", provided at least two HMF units are linked by a carbon-carbon bond with involvement of an aromatically bound carbon atom at position 3 or 4 of the furan ring of one of the two HMF units.

According to an advantageous configuration of the invention, the aromatically bound carbon atom of the first unit is linked to the aldehyde carbon atom of the second HMF unit.

Figure 1:
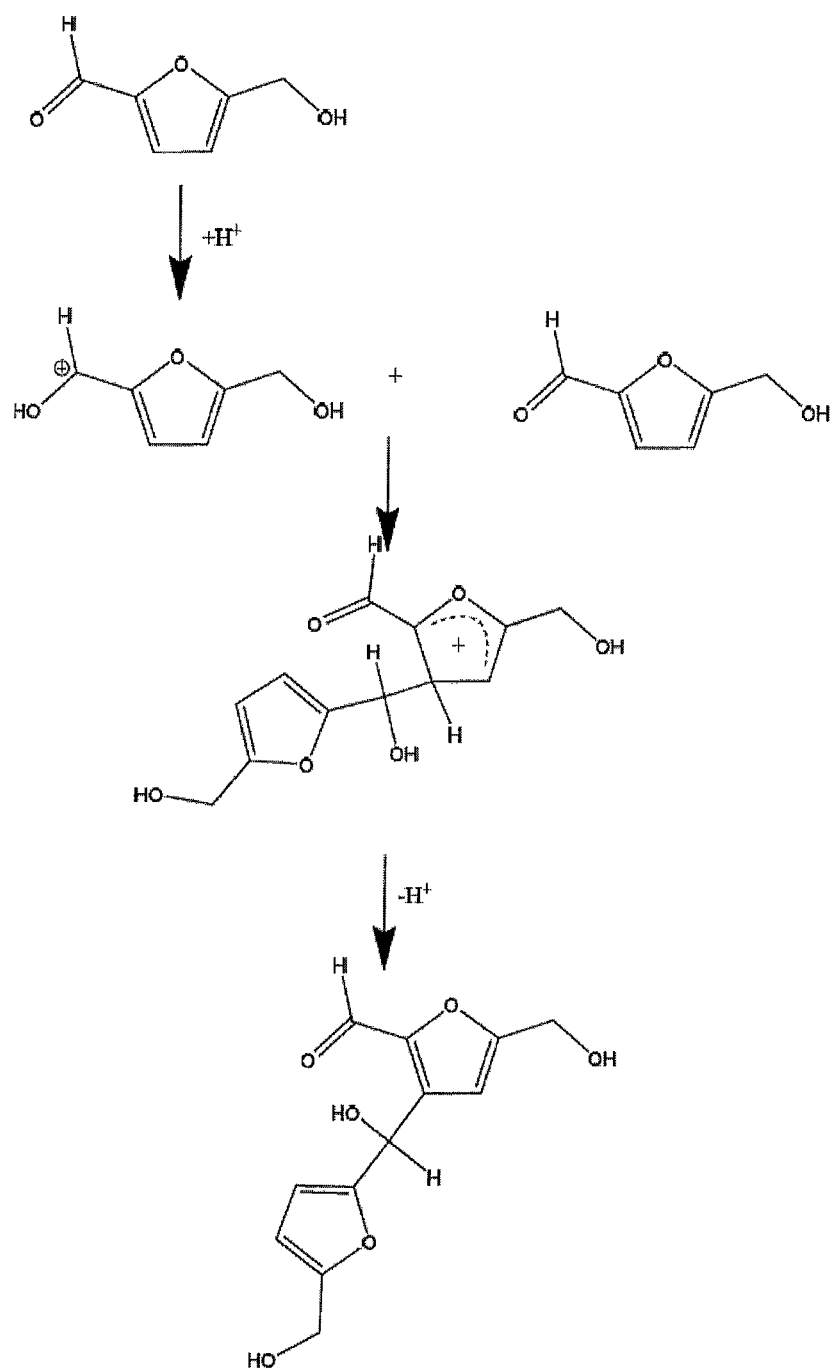
FIG. 1 shows a proposed mechanism of the carbon-carbon bond formation under acid conditions on the basis of the dimerization of two HMF molecules.
Figure 2:
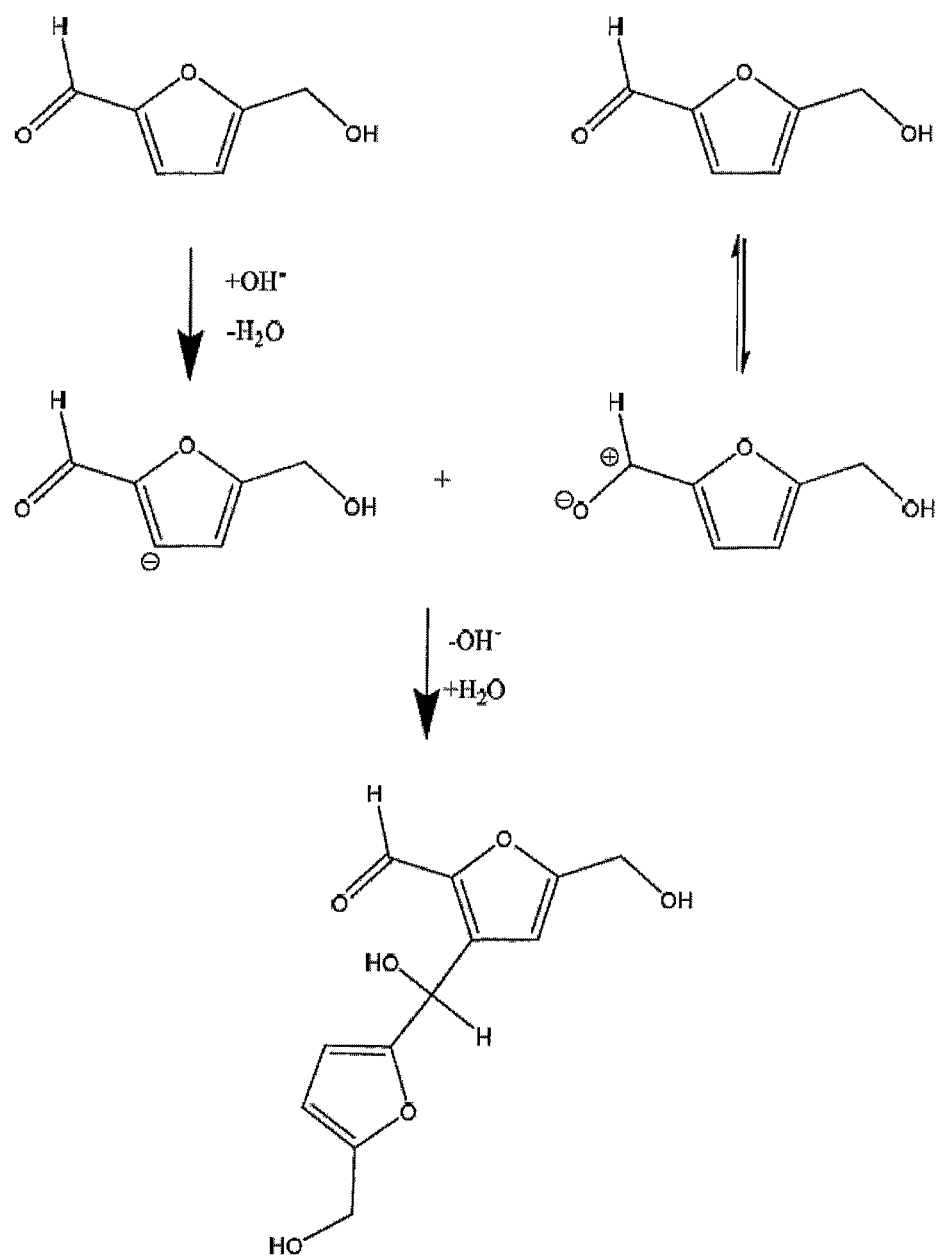
FIG. 2 shows a proposed mechanism of the carbon-carbon bond formation under basic conditions on the basis of the dimerization of two HMF molecules.

The mechanisms proposed for the formation of a carbon-carbon bond that takes place with involvement of aromatically bound carbon atom and aldehyde carbon atom under acidic conditions and under basic conditions are presented in FIGS. 1 and 2. From these mechanisms, it is evident among other facts that HMF oligomers having a link via a carbon-carbon bond at the same time also have more free functional aldehyde and/or hydroxyl groups than do HMF oligomers in which the bond is formed merely via aldehyde and/or hydroxyl groups of the HMF. For this reason, a higher degree of cross-linking, which is based on the additional carbon-carbon bond, is then also favored, whereby a higher density of free aldehyde and hydroxy groups can be attained in an HMF oligomer.

According to a further advantageous configuration of the invention, the carbon-linked HMF oligomer has 2 to HMF 20 units, preferably 2 to 10 HMF units, particularly preferably 2 to 4 HMF units. HMF oligomers with 2 to 10 units are readily water-soluble under moderate conditions, meaning room temperature and normal pressure.

According to a further advantageous configuration of the invention, the carbon-linked HMF oligomer contains, besides the first and second HMF units linked with involvement of an aromatically bound carbon, at least one further unit, which is linked to an HMF unit with formation of an ether, hemiacetal or acetal bond.

A further subject matter of the present invention is a process for the manufacture of the carbon-linked HMF oligomers, wherein the process includes treating an aqueous suspension of cellulose-containing biomass and/or an aqueous carbohydrate solution of at least one hexose and/or one aqueous 5-hydroxymethylfurfural solution under hydrothermal conditions.

The treatment of biomass, such as plant-based raw materials, of carbohydrates or of compounds derived from carbohydrates under hydrothermal conditions for the production of 5-HMF (monomers) is known, and it provides for exposing the starting material to pressure and elevated temperature in aqueous medium. The inventors have found that, during the treatment of an aqueous suspension of cellulose-containing biomass and/or of an aqueous carbohydrate solution of at least one hexose and/or one aqueous 5-hydroxymethylfurfural solution under hydrothermal conditions, carbon-linked HMF oligomers are formed.

Cellulose-containing biomass, which frequently accumulates as a waste product of the agricultural producers, is particularly preferred because of its low cost factor. Preferred hexoses are fructose or glucose; in particular, they may be fructose or mixtures of fructose and glucose.

Preferred hydrothermal conditions are saturated-steam pressure and temperatures of 150° C. to 250° C. These conditions have the advantage that the formation of HMF oligomers is completed within minutes to a few hours, depending on the starting material.

A further subject matter of the present invention is a process for the manufacture of the carbon-linked HMF oligomers, wherein the process includes exposing a more or less pure solution of HMF monomers and/or HMF oligomers to conditions that lead to the formation of HMF oligomers. Preferably, the conditions to which the HMF solution is exposed comprise an alkalinization or acidification and/or a heating of the solution.

The inventors have found that aqueous HMF solutions that were prepared, for example, from crystalline HMF with water, age with formation of the HMF oligomers. In this connection, the quantity and the molecular mass of the HMF oligomers may be determined using analytical means familiar to the person skilled in the art, such as HPLC and NMR spectroscopy.

The formation of HMF oligomers under moderate conditions, meaning at normal pressure and room temperature, may last in the range of hours, days or weeks. The aging process can be accelerated by acidification, alkalinization and heating.

Preferably, the process for the manufacture is carried out until the desired quantity of carbon-linked HMF oligomer is reached or until the reaction has stopped.

In this connection, it is self-evident for the person skilled in the art that the manufacture of the carbon-linked HMF oligomer by hydrothermal treatment can be combined with the manufacture of the carbon-linked HMF oligomer by aging. Thus, for example, an aqueous solution obtained from a hydrothermal treatment can then be aged at normal pressure.

Preferably, the at least one carbon-linked HMF is present in aqueous solution at the end of the manufacturing.

It is further preferable to influence the content, the size and/or the concentration of the carbon-linked HMF oligomer or of the carbon-linked HMF oligomers. Particularly preferably, the content of the carbon-linked HMF oligomer or of the carbon-linked HMF oligomers is influenced by subjecting a solution containing carbon-linked HMF oligomers to a filtration on at least one filtration means. The treatment, by filtration, of an aqueous HMF solution after a hydrothermal carbonization is described in DE 10 2014 112 240 A1, for example.

The carbon-linked HMF oligomers are very well suited as components in thermally curable resins. These resins are preferably obtained by the polycondensation of phenolic compounds and/or aminoplastic forming agents with reactive carbonyl compounds, especially aldehydes. Amino resins with the aminoplastic forming agents urea, melamine and dicyandiamide, phenol resins or aminophenol resins may be mentioned as examples. A thermosetting plastic material is obtained by subsequent curing of the resins.

The carbon-linked HMF oligomers are very reactive and have additional cross-linking capabilities. They are very effective as reactive carbonyl compounds in thermally curable resins. The resins obtained are distinguished by particularly good processing properties, such as a very high reactivity. A great advantage of the use of carbon-linked HMF oligomers for the manufacture of thermally curable resins is that reactive carbonyl compounds that are hazardous to health, such as formaldehyde, may be dispensed with completely.

The manufacture of the thermally curable resins by polycondensation is performed in a way known in itself. Suitable solvents as well as suitable reaction conditions such as reaction temperature and pH are in principle known to the person skilled in the art. Preferably, the reaction is carried out in an aqueous solvent.

The carbon-linked HMF oligomers may be used in mixtures with further reactive carbonyl compounds. Preferably at least one HMF oligomer is used in a mixture with at least one HMF monomer and/or with at least one further HMF oligomer containing ether, hemiacetal and/or acetal bonds. Even small quantities of carbon-linked HMF oligomer are sufficient to prepare very reactive carbonyl compounds.

The carbon-linked HMF oligomers are suitable in particular for the manufacture of composite materials from lignocellulose-containing material, such as wood shavings, wood fibers or wood chips. The manufacture of the wood composite materials takes place according to generally known methods in this technical field. The wood composite materials can be obtained by bringing the lignocellulose-containing material into contact with thermally curable resins containing carbon-linked HMF oligomers, and then curing the resins, which is associated with a cross-linking. Preferably, the curing is undertaken by pressing the resin provided with the lignocellulose-containing material.

The following examples serve merely as the explanation of the invention and are not intended to restrict it in any way.

EXAMPLE 1

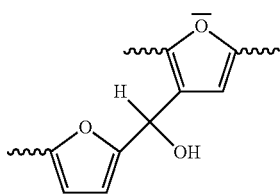

Example 1 shows a part of a carbon-linked HMF oligomer containing a structural element, which comprises a carbon-carbon bond with involvement of an aromatically bound carbon atom of the furan ring of a first HMF unit and the aldehyde-group carbon atom of a second HMF unit.

For clarity, a part of the carbon-linked HMF oligomer is shown, as indicated by the curved lines. Terminal HMF units, not illustrated in Example 1, are preferably bounded by aldehyde groups or hydroxymethyl groups.

EXAMPLE 2

Manufacture of Chipboard Panels a) Preparation of an HMF solution containing HMF oligomers:

A 16% aqueous solution of crystalline HMF was simultaneously concentrated and aged by reducing the volume in a rotary evaporator at 45° C. and 30 mbar until the concentration of HMF was 50 wt % relative to the solution.

b) Preparation of urea-HMF resins and comparison of the properties:

Two resins differing in their mole ratio of urea to HMF were prepared. A first resin, denoted in the following by UH(1:0.5), was prepared with a ratio of urea to HMF of 1:0.5. A second resin, denoted in the following by UH(1:0.25), was prepared with a ratio of urea to HMF of 1:0.25. The solids content of the resins was approximately 58%. For both resins, 400 mL of the 50% HMF solution from a) was used. For both resins, the urea was reacted with HMF at a pH of 2, for 2.5 hours and a temperature of 90° C. at first and then for several hours at a temperature of 20° C. In the process, the change of the viscosity of the resins was observed.

TABLE 1

Increase of viscosity as a function of time

| | Viscosity [mPa · s] | |
|---|---|---|
| Time [hours] | UH(1:0.5) | UH(1:0.25) |
| 4 | 470 | — |
| 24 | 1275 | 58 |
| 48 | — | 60 |
| 120 | — | 65 |
| 144 | — | 65 |
| 168 | — | 65 | c) Pressing of wood shavings to chipboard panels:

The resin UH(1:0.5) with a viscosity of 1275 mPa·s and the resin UH(1:0.25) with a viscosity of 65 mPa·s were used for the subsequent pressing of wood shavings. The resins were mixed respectively with the wood shavings and with hexamethylenetetramine and then pressed at 220° C. for the production of panels measuring 250 mm×250 mm×16 mm. The loading of the dry wood was 10 wt % resin solid relative to the quantity of wood. In order to test the influence of various press times and various quantities of curing agent, several panels were produced with variation of the times and of the quantities of hexamethylenetetramine. The values obtained for the chipboard panels with the two resins UH(1:0.5) and UH(1:0.25) are presented in Table 2.

For comparison, a third resin, UH45(1:0.5), was produced by reacting the components of the resin UH(1:0.5) at a lower temperature of 45° C. The resin UH45(1:0.5) was also used for the pressing of wood shavings to chipboards measuring 250 mm×250 mm×16 mm. The values obtained for these chipboard panels are also presented in Table 2.

The comparison of the panels produced with the resins showed that, in principle, better values of the internal bond strength are obtained at a longer press time.

With a mole ratio of urea to HMF of 1:0.5, the panels 3 and 4 attained the high values of 52 N/mm² and 55 N/mm². These values can be attributed to a press time of 7.5 minutes in association with a high temperature of 90° C. for preparation of the resins.

The panels 1 and 2 as well as 5 and 6 illustrate the influence of temperature during the preparation of the resins.

Even panels produced with smaller quantities of HMF yield a satisfactory result when the press time is prolonged, as shown by panels 7 to 10.

As regards the curing agent, it was found that different quantities of curing agent are slightly noticeable to unnoticeable, provided the panels were produced with a certain proportion of HMF, as shown by panels 3 to 6. The panels 7 and 10, with lower proportions of HMF, are clearly influenced more strongly by the quantity of curing agent. The values illustrate that, as a consequence of the positive properties of the HMF oligomers used, the needed quantities of curing agent can be reduced drastically to obtain nonetheless products with identical or comparable internal bond strength.

Internal Bond Strength (IB) in Accordance with NF EN 319 (AFNOR 1993)

The internal bond strength in [N/mm²] is expressed by the following formula:

$$IB = \frac{F\max}{a \times b},$$

where FMax is the force at break, a the width and b the length of the panel.

For chipboard and fiberboard panels with a thickness in the range of 13 mm to 20 mm, NF EN 319 (AFNOR 1993) specifies an internal bond strength of ≥0.35 N/mm².

The panels for investigation of the internal bond strength were obtained by cutting out of the panels produced under c). Their size was 50 mm×50 mm. Prior to the cutting, the panels were stabilized in a dryer at 20° C. and a relative humidity of 65%.

The panels were fastened to a backing by means of a hot-melt adhesive. The determination of the internal bond strength was performed mechanically, perpendicular to the plane of the panels, in accordance with NF EN 319 (AFNOR 1993).

All features of the invention can be essential to the invention both individually as well as in any combination whatsoever with one another.

Although several embodiments of the present invention have been shown and described, it is to be understood that many changes and modifications may be made thereunto without departing from the spirit and scope of the invention.

What is claimed is:

1. A carbon-linked hydroxymethylfurfural oligomer comprising a first hydroxymethylfurfural unit and a second hydroxymethylfurfural unit, wherein the first hydroxymethylfurfural unit and the second hydroxymethylfurfural unit are linked by a carbon-carbon bond with involvement of an aromatically bound carbon atom at position 3 or position 4 of a furan ring of the first hydroxymethylfurfural unit.

2. The hydroxymethylfurfural oligomer according to claim 1, wherein the aromatically bound carbon atom of the first hydroxymethylfurfural unit is linked to an aldehyde carbon atom of the second hydroxymethylfurfural unit.

3. The hydroxymethylfurfural oligomer according to claim 1, wherein the hydroxymethylfurfural oligomer has 2 to 20 hydroxymethylfurfural units.

4. The hydroxymethylfurfural oligomer according to claim 1, wherein the hydroxymethylfurfural oligomer has 2 to 10 hydroxymethylfurfural units.

5. The hydroxymethylfurfural oligomer according to claim 1, wherein the hydroxymethylfurfural oligomer has 2 to 4 hydroxymethylfurfural units.

6. The hydroxymethylfurfural oligomer according to claim 1, wherein the hydroxymethylfurfural oligomer further comprises at least one further unit linked to the first hydroxymethylfurfural unit or the second hydroxymethylfurfural unit with formation of an ether bond, a hemiacetal bond or an acetal bond.

7. A process for manufacturing a thermally curable resin comprising:
   (a) providing a hydroxymethylfurfural oligomer according to claim 1; and
   (b) using the hydroxymethylfurfural oligomer to manufacture the thermally curable resin.

8. A process for manufacturing a composite material comprising:
   (a) providing a hydroxymethylfurfural oligomer according to claim 1; and

TABLE 2

Parameters of the production of chipboard panels, and properties of the chipboard panels

| Panel | Resin | Synthesis temperature [° C.] | Viscosity [mPa · s] | Mole ratio of urea to HMF | Press temperature [° C.] | Press time [min] | Curing agent [%] | Density [kg/m²] | Internal bond strength (IB) [N/mm²] |
|---|---|---|---|---|---|---|---|---|---|
| 1 | UH45(1:0.5) | 45 | 382 | 1:0.5 | 220 | 5.5 | 5 | 733 | 0.27 |
| 2 | UH45(1:0.5) | 45 | 382 | 1:0.5 | 220 | 5.5 | 2.5 | 729 | 0.21 |
| 3 | UH(1:0.5) | 90 | 1275 | 1:0.5 | 220 | 7.5 | 5 | 717 | 0.55 |
| 4 | UH(1:0.5) | 90 | 1275 | 1:0.5 | 220 | 7.5 | 2.5 | 718 | 0.52 |
| 5 | UH(1:0.5) | 90 | 1275 | 1:0.5 | 220 | 5.5 | 5 | 715 | 0.43 |
| 6 | UH(1:0.5) | 90 | 1275 | 1:0.5 | 220 | 5.5 | 2.5 | 718 | 0.43 |
| 7 | UH(1:0.25) | 90 | 65 | 1:0.25 | 220 | 7.5 | 5 | 714 | 0.44 |
| 8 | UH(1:0.25) | 90 | 65 | 1:0.25 | 220 | 6.5 | 5 | 715 | 0.39 |
| 9 | UH(1:0.25) | 90 | 65 | 1:0.25 | 220 | 5.5 | 5 | 712 | 0.31 |
| 10 | UH(1:0.25) | 90 | 65 | 1:0.25 | 220 | 7.5 | 2.5 | 713 | 0.36 |

(b) using the hydroxymethylfurfural oligomer to manufacture the composite material from a lignocellulose-containing material.

\* \* \* \* \*